United States Patent [19]

Burston

[11] Patent Number: 4,907,588

[45] Date of Patent: Mar. 13, 1990

[54] LASER SYSTEM WITH LASER ACTUATION MEANS

[76] Inventor: Ronald J. Burston, 5 Auchengate, Barassie, Troon, Ayrshire, Scotland, KA106V9

[21] Appl. No.: 264,417

[22] Filed: Oct. 31, 1988

[30] Foreign Application Priority Data

Oct. 31, 1987 [GB] United Kingdom ............. 8725566

[51] Int. Cl.⁴ .............................................. A61B 17/36
[52] U.S. Cl. .................................. 606/11; 128/395
[58] Field of Search ................ 128/303.1, 395–398, 128/6; 219/121.61

[56] References Cited

U.S. PATENT DOCUMENTS

| | | | |
|---|---|---|---|
| 4,414,608 | 11/1983 | Furihata | 128/6 |
| 4,433,675 | 2/1984 | Konoshima | 128/6 |
| 4,525,164 | 6/1985 | Loeb et al. | 128/DIG. 12 |
| 4,608,980 | 9/1986 | Aihara | 128/303.1 |
| 4,658,817 | 4/1987 | Hardy | 128/303.1 |
| 4,716,288 | 12/1987 | Doi | 128/303.1 |
| 4,722,337 | 2/1988 | Losch et al. | 128/395 |

*Primary Examiner*—Max Hindenburg
*Attorney, Agent, or Firm*—Bell, Seltzer, Park & Gibson

[57] ABSTRACT

A laser system 10 has a laser source 11 which is arranged to emit a high power parallel laser light beam along an optical axis 12 concentric with a socket which is designed slidingly to receive a laser launch system 20. The system 20 includes a focussing lens, is replaceably secured to the socket by means of a spring loaded latch 21, and is arranged to receive a fibre delivery system 25 having a single optical fibre along which focussed laser radiation is directed. Source 11 is controlled in wavelength and power output by a switching arrangement 44 actuated by actuator 45 which carry coded information concerning the particular optical configuration of the systems 20, 25.

10 Claims, 1 Drawing Sheet

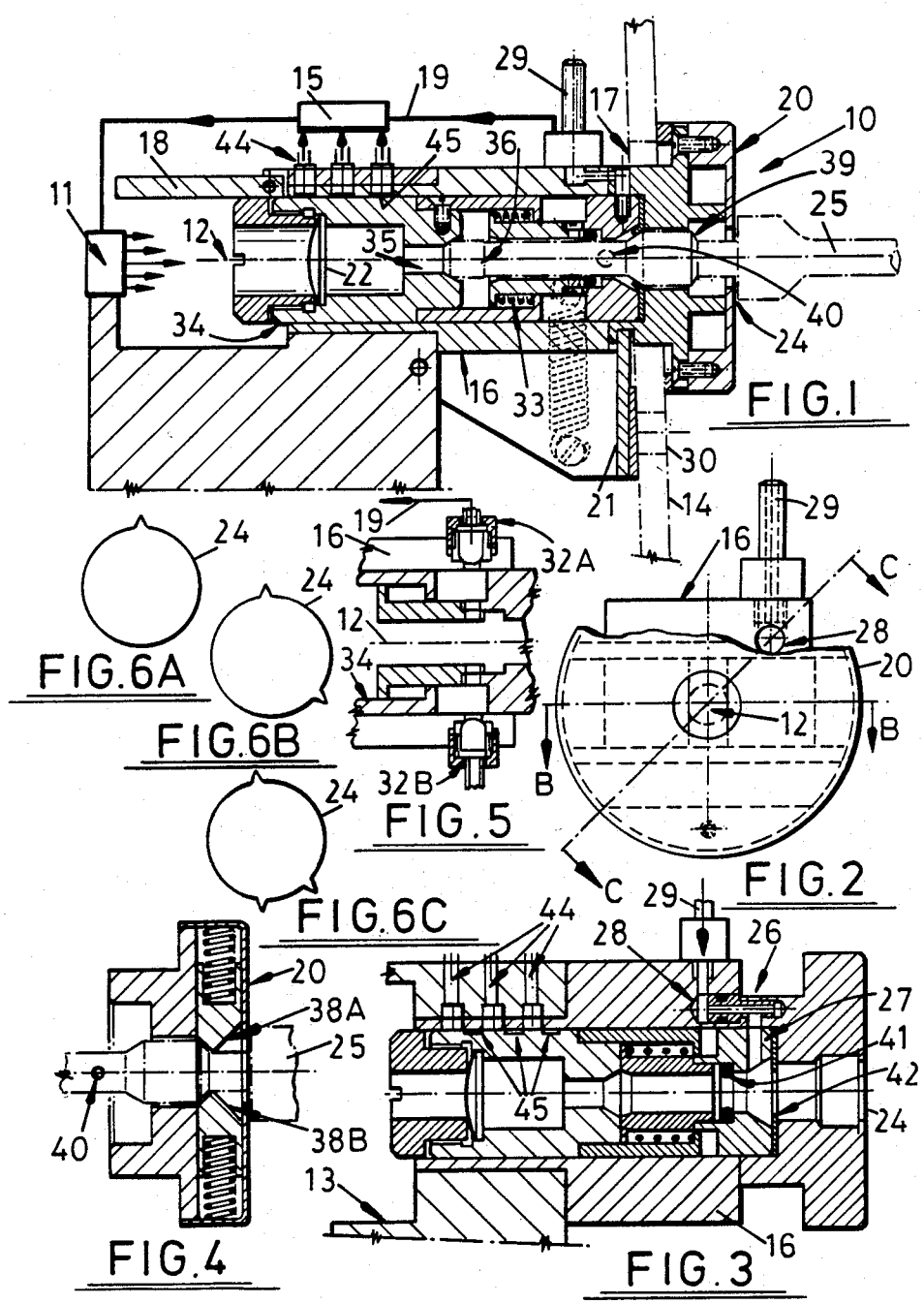

LASER SYSTEM WITH LASER ACTUATION MEANS

This invention relates to a laser system.

In medical work increasing use in being made of high power laser radiation which is controlled in wavelength and energy and is delivered to a site on or within a human or animal body by an optical fibre assembly incorporating a single optical fibre (with or without attachments), laser radiation being delivered to the optical fibre assembly by a laser system having a launch assembly incorporating a convex lens for coupling the optical fibre assembly to the laser radiation source in a position critical manner, it being well known that absence of position critical coupling results in degradation of the fibre in the fibre assembly.

Such forms of laser system require to be versatile for providing at the work site laser radiation of differing divergencies and power densities to accord with the best work practices in the medical field and it is an object of the present invention to provide a new and improved form of laser system capable of fulfilling these requirements.

According to the present invention there is provided a laser system having a housing containing a laser source adapted to emit a high energy parallel laser light beam along an optical axis, the laser source being mounted on a rigid support, first socket means having a socket axis aligned with said optical axis mounted on said support and extending between the laser source and an opening in said housing, second socket means replaceably secured in the first socket means, said second socket means being slidingly insertable and removable from within the first socket means through said housing opening and forming a laser launch system comprising a tubular main body portion containing at the end remote from said opening a convergent lens aligned with the optical axis for focussing the parallel laser light beam, the end of said main body portion adjacent said opening protruding therefrom and being adapted releasably to receive an optical fibre delivery system incorporating a single optical fibre having an end face which is critically positioned with respect to the convergent lens to receive focussed laser radiation characterised in that said first socket means comprises switching means connected to control operation of the laser source and said systems comprise means arranged for actuating said switching means when said systems are co-operatingly engaged with each other within the first socket means, said actuating means carrying coded information concerning the particular optical configuration of the systems.

A spring-loaded mechanical latch may be provided for restraining removal of the launch system from the first socket means, the latch being releasable via a tool insertable through an aperture in the housing adjacent said opening.

Preferably the first socket means incorporates a gas supply passageway extending parallel to the socket axis and opening into the housing aperture and the launch system has a spigot adapted to enter the passageway, said spigot having a bore in communication with the bore of said main body portion to enable gas to be supplied thereto from the gas supply passageway, and the external surface of the spigot carries an O-ring seal for sealing the spigot into the passageway, the spigot having a substantially smaller outside diameter than that of the main body portion whereby unique angular orientation of the main body portion in the first socket means is achieved with ease of gas sealing localised to the spigot.

Either the launch system or the delivery system may incorporate the means for actuating said switching devices, said switching devices being connected to control operation of the laser source which may have the capability of multiple wavelength operation. The switching devices may be adapted to inhibit emission of laser radiation from the laser source in the absence of actuation by said actuating means. Additionally, or alternatively, the switching devices may be adapted to select the wavelength and/or limit the power output of the laser source to a level predetermined by the particular form of actuating means, there being different forms of actuating means for launch and delivery systems having different optical configurations.

The switching devices may be opto emitter/receiver devices in which case the actuating means may comprise optical reflection determining devices. The opto-reflection determining devices may be highly reflective and/or highly absorbent of radiation emitted by the emitter/receiver devices. Alternatively the switching devices may be micro-switches.

It is preferred that the end of the main body portion adjacent said opening has a mouth, the perimeter of which is asymmetric, being adapted to receive an optical fibre delivery system having a corresponding asymmetric transverse cross sectional shape in at least that part of the delivery system which mates with said mouth, the shape of said permiter being predetermined according to the particular nature of the launch system to codify the maximum power level and/or wavelength transmitted thereby.

Preferably the asymmetric transverse cross sectional shape of the optical fibre delivery system enables the delivery system to fit the various asymmetric perimeters of said mouth indicating power levels up to and including the maximum power level of the fibre delivery system.

By virtue of the present invention the laser system is rendered user-friendly and is provided with the automatic capability of selecting and controlling wavelength and maximum power output of the laser source for both patient safety and user/equipment safety.

An embodiment of the present invention will now be described by way of example with reference to the accompanying drawings, in which:

FIG. 1 is a cross sectional and partly schematic view of a laser system according to the present invention and in the presence of a fibre delivery system;

FIG. 2 is an axial view taken from one end of FIG. 1 with parts omitted in the interests of clarity;

FIG. 3 is a sectional view taken on line C—C in FIG. 2 in the absence of a fibre delivery system;

FIG. 4 is a scrap sectional view of a first detail taken on the line B—B in FIG. 2;

FIG. 5 is a scrap sectional view of a second detail taken on the line B—B in FIG. 2; and FIGS. 6A, 6B, 6C, illustrate alternative forms of a third detail.

A laser system 10 is illustrated in the accompanying drawings having a laser source 11 which is arranged to emit a laser light beam along an optical axis 12. Source 11 is mounted on a rigid support 13 within a housing 14 only part of which is shown in FIG. 1. Operation of laser source 11 is under the control of a controller 15, as will be explained. Also mounted on support 13 and located within the housing 14 is a structure 16 which defines a socket having its axis aligned with optical axis 12. The structure 16 terminates at an opening 17 in the housing 14 and at its end adjacent laser source 11 the structure 16 includes a mechanical shutter 18 which is pivotally mounted and actuated by gravity to block transmission of laser radiation from source 11 into the socket of structure 16 when the socket is empty. The socket of structure 16 is designed slidingly to receive a laser launch system 20 in the manner shown in FIG. 1, the system 20 being replaceably secured to the structure 16 by means of a spring loaded latch 21 pivotally mounted on support 13 such that the system 20 protrudes from opening 17 of housing 14. The system 20 has a main body portion which is tubular and at the end adjacent laser source 11 has a convergent lens 22 aligned with optical axis 12 and at the end adjacent opening 17 has a mouth 24 for receiving an optical fibre delivery system 25.

The launch system 20 in addition to its tubular main body portion previously described incorporates a relatively small diameter spigot 26 which has a bore 27 communicating with the bore of the main body portion adjacent mouth 24. This spigot 26 is arranged to fit a passageway 28 formed in the structure 16 and which forms part of a gas supply arrangement 29. Spigot 26 carries an O-ring seal so that the spigot sealingly engages the passageway 28 and because the spigot 26 is spaced from the main body portion of system 20 and co-axial therewith the system 20 is easy to fit to the socket formed by structure 16 and gas sealing is easily achieved due to the relatively small diameter of the spigot 26. Latch 21 is operable by a tool (not shown) such as a small diameter pin which penetrates housing 14 at an aperture 30 adjacent opening 17.

Structure 16 incorporates an optical interlock for laser source 11 to prevent source 11 emitting radiation in the absence of a system 20. This interlock as shown in FIG. 5 comprises a light emitting/receiving pair 32A, 32B, providing an output signal on control line 19 leading to controller 15.

The launch system 20 in its main body portion is formed by two telescopically connected parts which are biassed by coil spring 33 to the condition where system 20 is of minimum axial length. The telescopic part 34 in which lens 22 is mounted in principally made of stainless steel and has a conical collar 35 which acts as an abutment and locating surface for the end 36 of fibre delivery system 25. When delivery system 25 is inserted into the socket bore end 36 which is made of brass abuts collar 35 causing telescopic displacement of part 34 against the bias of spring 33 and such displacement is continued until such time as the spring loaded detents 38A, 38B, shown in FIG. 4 snap behind the shoulder 39 formed on the handle of delivery system 25. When this occurs end 36 is critically located with respect to lens 22 in both axial separation and concentricity or axial alignment and the gas supply arrangement 29 delivers gas through passageway 28 and bore 27 to a part of the bore at which the handle of the delivery system 25 is provided with a gas supply aperture 40. This part of the bore is determined by seals 41 and 42 forming part of system 20, as shown in FIG. 3, and which are engaged by the handle of delivery system 25 on opposite sides of gas supply aperture 40.

For the purpose of further controlling laser source 11 the structure 16 is additionally provided with several switching devices 44 which are operable by actuators 45 mounted on part 34 of launch system 20. In this embodiment each device 44 is an opto emitter/receiver and each actuator is an optical reflection determining element and there are three devices 44 and three devices 45. The outputs of devices 44 are delivered to controller 15 and in the absence of a delivery system 25 fitted to assembly 20, as is shown in FIG. 3, the actuating devices 45 are axially displaced from switching devices 44 which in that condition are arranged as a further electrical isolating arrangement to prevent laser source 11 emitting laser radiation. In the condition illustrated in FIG. 1 when part 34 has been axially displaced by virtue of the presence of delivery system 25, the actuating devices 45 are substantially aligned with switching devices 44, there being no particular criticality in this alignment and in this condition switching devices 44 are arranged to provide a coded signal to controller 15 as determined by the particular nature of the individual actuating devices 45 in order to determine the operating wavelength and/or maximum power output of laser source 11 to match that wavelength and power output to the particular nature of lens 22 in the particular assembly 20 which is fitted in the system 10. This is achieved by the actuating devices 45 having different reflective capabilities and by the particular order of these reflective capabilities in the axial direction.

In this connection it will be understood that the purpose of having system 20 replaceably mounted in the structure 16 is to permit fitting of different forms of system namely, systems having different forms of lenses 22 since these lenses determine the cone angle of the radiation launched into the delivery system 25 and thereby determine the nature of the radiation delivered at the work site by the system 25 and each system 20 is a close sliding fit in the bore formed by structure 16 to ensure concentricity of lens 22 with optical axis 12.

It will be appreciated that different forms of delivery system 25 may be utilised wherein the single fibre has a particular power level limit associated with fibre diameter (or attachments to the fibre delivery system, e.g. a focussing handpiece or micromanipulator). This arises because delivery systems 25 are preferably disposable to prevent cross-contamination of patients and cost effective manufacture is therefore highly desirable. For a particular work practice where the power level of the laser radiation is restricted from the maximum possible capable of being emitted by laser source 11 a relatively inexpensive fibre can be used in delivery system 25. The higher the power level to be transmitted by the fibre the more expensive is the fibre. Accordingly mouth 24 of system 20 is provided with an asymmetric perimeter as illustrated in FIGS. 6A, 6B and 6C, these being respectively arranged to conform with and denote the maximum power level capable of being transmitted by the lens 22. Correspondingly the cross sectional shape of that part of the delivery system which mates with mouth 24 is provided with an identical asymmetric transverse cross section and very high power transmitting fibres are provided with the FIG. 6A shape, for example, which can be fitted to the FIG. 6B shape or the FIG. 6C shape, both of which denote lower orders of power level, but the FIG. 6B shape cannot be fitted to the FIG. 6A shape since the power level of the FIG. 6A shape would be greater than that denoted by the FIG. 6B shape. The FIG. 6B shape can, however, be fitted to the FIG. 6C shape since the latter denotes a power level which is lower than that of the FIG. 6B shape.

Additionally or alternatively part of the fibre delivery system 25 which enters into the bore of the launch system 20 may be provided with actuators similar to actuating devices 45 and arranged to operate the switching devices 44 in addition to or instead of devices 45 so that the laser source 11 is controlled in operation in accordance with the particular optical configuration of both systems 20, 25 fitted to the structure 16.

In the interests of clarity FIG. 2 illustrates that structure 16 is externally square in cross section and denotes the location of the gas supply arrangement 29. The socket formed by structure 16 has a circular bore for receiving system 20. By way of example fibre delivery system 25 may take any one of the forms described in British Pat. Specification No. 2177518.

It will be appreciated from the foregoing that the fibre elivery system 25 is adapted to fit within a channel of an endoscope for use in medical work and because the overall outside diameter of the endoscope is severly restricted so is the outside diameter of the system 25. Accordingly, there is a need to use small diameter optical fibres and the launch optical system and the fibre type (plastics-clad glass core) need to be matched to the laser wavelength and output power. As previously explained the laser preferably can be operated at any one of several wavelengths.

I claim:

1. A laser system having a housing containing a laser source capable of emitting a high energy parallel laser light beam along an optical axis, the laser source being controlled in operation by a controller and mounted on a rigid support, first socket means having a socket axis aligned with said optical axis mounted on said support extending between the laser source and an opening in said housing, second socket means replaceably secured in the first socket means, said second socket means being slidingly insertable and removable from within the first socket means through said housing opening and comprising a tubular main body portion containing a convergent lens aligned with the optical axis for focussing the parallel laser light beam whereby to form a laser radiation launch system the end of said main body portion adjacent said opening protruding therefrom and releasably receiving an optical fibre delivery system incorporating a single optical fibre having an end face which is critically positioned with respect to the convergent lens to receive focussed laser radiation, wherein said first socket means comprises switching means connected to said controller and said launch and delivery systems comprise actuating means arranged for selectively actuating said switching means when said launch and delivery systems are co-operatingly engaged with each other within the first socket means, said actuating means carrying coded information concerning the particular optical configuration of the launch system and which effects the selective actuation of the switching means.

2. A laser system as claimed in claim 1 wherein the laser source has the capability of multiple wavelength operation and the switching means are arranged to control the wavelength and/or limit the power output of the laser source to a level predetermined by the particular form of actuating means, there being different forms of actuating means for launch systems having different optical configurations.

3. A laser system as claimed in claim 1 wherein the switching devices are arranged to inhibit emission of laser radiation from the laser source in the absence of actuation by said actuating means.

4. A laser system as claimed in claim 1 wherein the switching means are opto emitter/receiver devices and the actuating means comprise optical reflection determining devices.

5. A laser system as claimed in claim 4 wherein the opto-reflection determining devices are either highly reflective or highly absorbent of radiation emitted by the emitter/receiver deivces.

6. A laser system as claimed in claim 1 wherein the switching means are micro-switches.

7. A laser system as claimed in claim 1 wherein the main body portion adjacent said opening has a mouth, the perimeter of which is asymmetric, being arranged to receive an optical fibre delivery system having a corresponding asymmetric transverse cross sectional shape in at least that part of the delivery system which mates with said mouth, the shape of said perimeter being predetermined according to the particular nature of the launch system to codify the maximum power level and/or wavelength transmitted thereby.

8. A laser system as claimed in claim 7 wherein the asymmetric transverse cross sectional shape of the optical fibre delivery system enables the delivery system to fit the various asymmetric perimeters of said mouth indicating power levels up to and including the maximum power level of the fibre delivery system.

9. A laser system as claimed in claim 1 including a spring-loaded mechanical latch for restraining removal of the second socket means from the first socket means, the latch being releasable via a tool insertable through an aperture in the housing adjacent said opening.

10. A laser system as claimed in claim 1, wherein said tubular main body portion comprises first and second telescopic portions and spring means resiliently urging said telescopic portions towards their minimal axial length condition, said actuating means are carried by said second telescopic portion, said first telescopic portion is releasbly secured to said first socket means adjacent said opening, said second telescopic portion comprises an abutment collar for said delivery system, said first telescopic portion comprises spring loaded detent means for said delivery system and in the absence of said delivery system said actuating means are axially displaced from said switching means and isolate the laser source from emitting laser radiation.

* * * * *